United States Patent [19]

Mitschke

[11] 4,144,290
[45] Mar. 13, 1979

[54] PRODUCTION OF BROMOARYL CHLOROPHOSPHATES

[75] Inventor: Karl-Heinz Mitschke, Odenthal, Fed. Rep. of Germany

[73] Assignee: Bayer Aktiengesellschaft, Leverkusen, Fed. Rep. of Germany

[21] Appl. No.: 848,413

[22] Filed: Nov. 3, 1977

[30] Foreign Application Priority Data

Nov. 23, 1976 [DE] Fed. Rep. of Germany ....... 2653095

[51] Int. Cl.$^2$ .............................................. C07F 9/14
[52] U.S. Cl. .................................... 260/986; 260/960
[58] Field of Search ................................. 260/986, 960

[56] References Cited

U.S. PATENT DOCUMENTS 2,057,600  10/1936  Thomson ............................ 260/986

OTHER PUBLICATIONS

Schulek et al., "Talanta", vol. 1 (1958), pp. 224–237.

Primary Examiner—Anton H. Sutto
Attorney, Agent, or Firm—Sprung, Felfe, Horn, Lynch & Kramer

[57] ABSTRACT

A process for the preparation of brominated aryl dichlorophosphates or diaryl chlorophosphates of the formula:

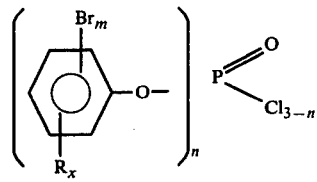

wherein
R each independently is hydrogen, an alkoxy radical or alkyl radical containing 1 to 10 C-atoms, a perfluoroalkyl radical containing 1 to 10 C-atoms, halogen, the group —NO$_2$, —SO$_3$H, Cl$_2$P(O)O— or Cl$_2$P(O)OC$_6$H$_4$- CR$'_2$—,
R$^1$ each independently is hydrogen or an alkyl radical containing 1 to 4 C-atoms,
x is an integer from 1 to 4,
n is 1 or 2, and
m is from 0.1 to 2, comprising reacting the corresponding aryl dichlorophosphates or diaryl chlorophosphates, with a substantially equimolar mixture of bromine and chlorine at a temperature between about −10° and 100° C. Advantageously the bromine and chlorine are present as bromine chloride, the reaction is carried out at about 10° to 60° C. and the proportions, time and temperature of reaction are such that the degree of bromination is about 0.1 to 0.8 mol of bromine per phenyl nucleus.

4 Claims, No Drawings

PRODUCTION OF BROMOARYL CHLOROPHOSPHATES

The present invention relates to a process for the preparation of brominated aryl chlorophosphates. The process according to the invention is particularly suitable for the preparation of slightly brominated aryl chlorophosphates, e.g. up to 2 bromine atoms per phenyl nucleus.

Bromoaryl chlorophosphates, meaning bromoaryl dichlorophosphates and bis(bromoaryl)-chlorophosphates, are used in the preparation of mixed phosphoric acid ester chlorides or mixed phosphoric acid triesters, which are primarily used as flameproofing agents for inflammable substances, in particular made of plastics materials and fibers, for example U.S. Pat. No. 3,898,307 and German DOS No. 2,146,988. .

For the preparation of the bromoaryl-dichloro-phosphates or bis(bromoaryl)-chlorophosphates, the reactions of phosphorus oxychloride with bromophenols in the molar ratio of 1:1 or 1:2 are described in the literature, e.g. Houben-Weyl, Methoden der organischen Chemie, Volume 12/2, page 215 or 279. However, a disadvantage is that bromophenols are difficult to obtain and that their reactions take place with substantially more difficulty than the reactions of the halogen-free phenols (Houben-Weyl, Methoden der organischen Chemie, Volume 12/2, page 279).

An object of the present invention is therefore to provide a simple and economical process for the preparation of brominated aryl dichlorophosphates and diaryl chlorophosphates.

The present invention provides a process for the preparation of aryl phosphates of the general formula:

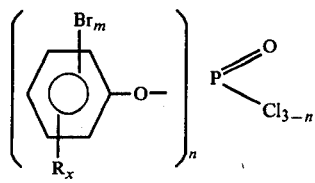

wherein
R each independently is hydrogen, an alkoxy radical or alkyl radical containing 1 to 10 C-atoms, a perfluoroalkyl radical containing 1 to 10 C-atoms, halogen, the group $-NO_2$, $-SO_3H$, $Cl_2P(O)O-$ or $Cl_2P(O)OC_6H_4-CR'_2-$,
R' each independently is hydrogen or an alkyl radical containing 1 to 4 C-atoms,
x is an integer from 1 to 4,
n is 1 or 2, and
m is from 0.1 to 2,
by brominating the corresponding aryl dichlorophosphates or diaryl chlorophosphates, which is characterized in that the aryl dichlorophosphates or diaryl chlorophosphates are reacted with a substantially equimolar mixture of bromine and chlorine, in particular with bromine chloride, at temperatures of between about −10 and 100° C.

It has been found that the bromination of aryl dichlorophosphates or diaryl chlorophosphates with mixtures of chlorine and bromine, in particular with bromine chloride, can be carried out particularly favorably. Above all, it was surprising that bromination could be carried out selectively even at relatively low temperatures. Whereas bromination is usually carried out at 80 to 100° C., it is carried out according to the invention at substantially lower temperatures without any significant chlorine substitution taking place and without requiring the presence of catalysts. By omitting catalysts, the subsequent purification of the reaction mixture, such as by distillation, can usually be omitted.

The process according to the invention is also suitable for brominating substituted aryl chlorophosphates such as, for example, alkyl-substituted aryl chlorophosphates. The halogenating agent does not appear to attack the alkyl groups in any case.

A halogen exchange at the P-Cl group by bromine is also not observed.

The process according to the invention is carried out in such a way that bromine and chlorine, in particular bromine chloride, are introduced into the aryl dichlorophosphates or diaryl chlorophosphates with stirring and cooling, without the addition of catalysts. Bromination is carried out at temperatures of between −10 and 100° C., preferably at about 10 to 60° C., particularly preferably at room temperature, for a period of about 0.5 to 7 hours. The reaction products formed are subsequently degassed in a vacuum by heating them to 90° C., and are distilled or are directly re-used.

The process may also be carried out in suitable solvents, such as for example in halogenated hydrocarbons or phosphorus oxychloride. This embodiment is suitable for relatively high-melting aryl dichlorophosphates or diaryl chlorophosphates; with liquid or low-melting aryl dichlorophosphates and diaryl phosphates the process is preferably solvent-free. The solvent may be admixed with the bromine chloride or bromine or chlorine or may also be applied together with the aryl dichlorophosphates or diaryl chlorophosphates.

The quantity of bromine introduced should advantageously be between about 0.05 and 1 mol, preferably between about 0.1 and 0.8 mol, per phenyl nucleus, depending upon the degree of bromination desired.

The process according to the invention may be carried out continuously, generally in several stages in a reaction cascade, as well as discontinuously. In the discontinuous process, the bromine chloride or bromine and chlorine are preferably introduced into the aryl dichlorophosphates or diaryl chlorophosphates.

Suitable starting materials for the process according to the invention include aryl dichlorophosphates and symmetrical or mixed diaryl chlorophosphates such as, for example, phenyl dichlorophosphate, cresyl dichlorophosphate, ethylphenyl dichlorophosphate, propylphenyl dichlorophosphate, butylphenyl dichlorophosphate, xylenyl dichlorophosphate, naphthenyl dichlorophosphate, diphenyl chlorophosphate, dicresyl chlorophosphate, bis-(ethylphenyl) chlorophosphate, bis-(propylphenyl)chlorophosphate, bis-(butylphenyl)-chlorophosphate, dixylenyl chlorophosphate, dinaphthenyl chlorophosphate, phenyl cresyl chlorophosphate and phenyl ethylphenyl chlorophosphate.

The process according to the invention is primarily suitable for the preparation of slightly brominated aryl dichlorophosphates and diaryl chlorophosphates. These slightly brominated aryl chlorophosphates (having a degree of bromination of up to 2 bromine atoms, preferably up to 0.8 bromine atoms, per phenyl nucleus) cannot be economically prepared from bromophenols or mixtures of bromophenols and phosphorus oxychloride by the formerly known processes. These slightly brominated aryl dichlorophosphates and diaryl chlorophosphates may now be prepared according to the invention in a simple manner.

The bromoaryl chlorophosphates prepared according to the invention may also even be reacted, for example with phenols, alcohols, alkylene oxides or amines, to form products having many uses, for example, flameproofing agents and plant protection agents.

The process according to the invention will now be illustrated in detail in the following examples:

EXAMPLE 1

1025 g (4.86 mol) of phenyl dichlorophosphate are placed in a three-necked flask equipped with a reflux condenser, a stirrer, an internal thermometer and a coolable dropping funnel having a feed pipe which terminates just above its base. The outlet of the reflux condenser is connected via a calcium chloride drying tube to a washing tower, in order to absorb the hydrogen chloride released during the reaction. The reaction temperature is maintained at 20 to 30° C. while 786 g (6.8 mol) of bromine chloride, pre-cooled to about −30° C., are added dropwise. After stirring for about 1 hour, the dissolved hydrogen chloride and unreacted bromine chloride or bromine and chlorine are removed under vacuum at 60 to 70° C. 1475 g of a mixture of compounds with the following average composition are obtained.

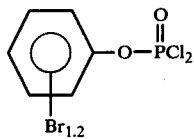

EXAMPLE 2

845 g (3 mol) of phenyl cresyl chlorophosphate are placed in a three-necked flask, equipped with a stirrer, a reflux condenser, a washing tower (as in Example 1), an internal thermometer and two dropping funnels whose outlets terminate just above the base of the vessel. The dropping funnel which is used for adding the chlorine has a cooling jacket and a dry-ice reflux condenser. 360 g (2.25 mol) of bromine and 160 g (2.25 mol) of chlorine are added dropwise at 20 to 30° C. with cooling, the dropping rate being selected in such a way that substantially equimolar quantities of both halogens are introduced per unit of time. The mixture is subsequently stirred for a further hour and the volatile constituents (hydrogen chloride, bromine chloride or bromine and chlorine) are removed by applying a vacuum and heating to 60 to 70° C. 1136 g of a product having the following average composition are obtained:

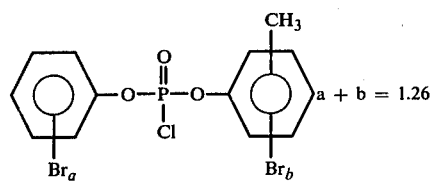

EXAMPLE 3

In accordance with the experimental arrangement in Example 1, 867 g of a mixture of the average composition:

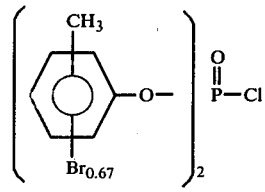

are obtained from 638 g (2.15 mol) of dicresyl chlorophosphate and 373 g (3.22 mol) of bromine chloride.

EXAMPLE 4

In accordance with the experimental arrangement in Example 1, 1324 g of a mixture of the average composition:

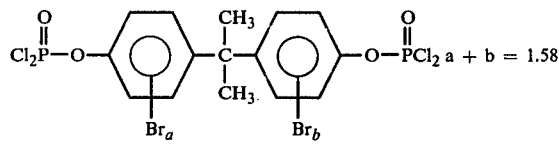

are obtained by reacting 1022 g (2.37 mol) of the compound:

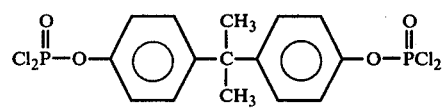

dissolved in 1000 ml of dichloroethane, with 683 g (5.92 mol) of bromine chloride, followed by distilling the solvent and removing the volatile constituents under vacuum at up to 70° C.

It will be appreciated that the instant specification and examples are set forth by way of illustration and not limitation, and that various modifications and changes may be made without departing from the spirit and scope of the present invention.

What is claimed is:

1. A process for the preparation of brominated aryl dichlorophosphates or diaryl chlorophosphates of the formula:

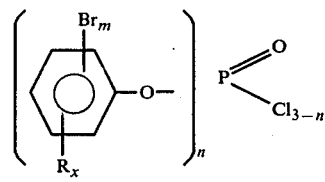

wherein

R each independently is hydrogen, an alkoxy radical or alkyl radical containing 1 to 10 C-atoms, a perfluoroalkyl radical containing 1 to 10 C-atoms halogen, the group $-NO_2$, $-SO_3H$, $Cl_2P(O)O-$ or $CL_2P(O)OC_6H_4-CR'_2-$, $R^1$ each independently is hydrogen or an alkyl radical containing 1 to 4 C-atoms, x is an integer from 1 to 4, n is 1 or 2, and m is from 0.1 to 2, comprising reacting the corresponding aryl dichlorophosphates or diaryl chlorophosphates with a substantially equimolar mixture of bromine and chlorine at a temperature between about −10 and 100° C.

2. A process according to claim 1, wherein the proportions, time and temperature of reaction are such that the degree of bromination is about 0.05 to 1 mol of bromine per phenyl nucleus.

3. A process according to claim 1, wherein the bromine and chlorine are present as bromine chloride, the reaction is carried out at about 10 to 60° C., and the proportions, time and temperature of reaction are such that the degree of bromination is about 0.1 to 0.8 mol of bromine per phenyl nucleus.

4. A process according to claim 1, wherein at least one R contains an alkyl or alkoxy radical.

* * * * *